US009689016B2

(12) United States Patent
Marcel et al.

(10) Patent No.: US 9,689,016 B2
(45) Date of Patent: Jun. 27, 2017

(54) METHOD FOR IN VIVO PRODUCTION OF DEGLYCOSYLATED RECOMBINANT PROTEINS USED AS SUBSTRATE FOR DOWNSTREAM PROTEIN GLYCOREMODELING

(71) Applicant: Caliber Biotherapeutics, LLC, Bryan, TX (US)

(72) Inventors: Sylvain Marcel, College Station, TX (US); Lindsay Bennett, College Station, TX (US)

(73) Assignee: Caliber Biotherapeutics, LLC, Bryan, TX (US)

(*) Notice: Subject to any disclaimer, the term of this patent is extended or adjusted under 35 U.S.C. 154(b) by 185 days.

(21) Appl. No.: 14/569,501

(22) Filed: Dec. 12, 2014

(65) Prior Publication Data

US 2015/0176045 A1 Jun. 25, 2015

Related U.S. Application Data

(60) Provisional application No. 61/917,793, filed on Dec. 18, 2013.

(51) Int. Cl.

| | |
|---|---|
| ***C12N 9/24*** | (2006.01) |
| ***C12P 21/00*** | (2006.01) |
| ***C07K 16/28*** | (2006.01) |
| ***C07K 16/00*** | (2006.01) |
| ***G01N 33/50*** | (2006.01) |

(52) U.S. Cl.

CPC ............ *C12P 21/005* (2013.01); *C07K 16/00* (2013.01); *C07K 16/2887* (2013.01); *C12N 9/2402* (2013.01); *C12Y 302/01096* (2013.01); *G01N 33/5008* (2013.01); *C07K 2317/14* (2013.01); *C07K 2317/41* (2013.01); *G01N 2440/38* (2013.01); *G01N 2500/04* (2013.01)

(58) Field of Classification Search

CPC ......... C07K 14/445; C07K 14/32; C12N 9/24

See application file for complete search history.

(56) References Cited

U.S. PATENT DOCUMENTS

| | | | |
|---|---|---|---|
| 7,338,933 | B2 | 3/2008 | DeFrees et al. |
| 7,696,163 | B2 | 4/2010 | DeFrees et al. |
| 7,956,032 | B2 | 6/2011 | DeFrees et al. |
| 8,361,961 | B2 | 1/2013 | DeFrees et al. |
| 2010/0173323 | A1 | 7/2010 | Strome et al. |
| 2013/0137857 | A1 | 5/2013 | Wang |

FOREIGN PATENT DOCUMENTS

| | | | |
|---|---|---|---|
| WO | 0200856 | A2 | 2/2002 |
| WO | 0236752 | A2 | 5/2002 |
| WO | 2010015722 | A1 | 2/2010 |
| WO | 2012170678 | A1 | 12/2012 |
| WO | 2013120066 | A1 | 8/2013 |

*Primary Examiner* — Maryam Monshipouri

(74) *Attorney, Agent, or Firm* — Edwin S. Flores; Chalker Flores, LLP

(57) ABSTRACT

The present invention includes compositions and methods of reducing the glycosylation of proteins comprising: obtaining a cell that expresses one or more proteins that comprise one or more glycosylation sites and are glycosylated; expressing in the cell one or more glycosidases that cleaves one or more glycosyl groups from the one or more proteins; and isolating the one or more proteins with reduced glycosylation from the cell.

15 Claims, 8 Drawing Sheets

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Ser Glu Lys Asp Glu Leu
1               5
```

METHOD FOR IN VIVO PRODUCTION OF DEGLYCOSYLATED RECOMBINANT PROTEINS USED AS SUBSTRATE FOR DOWNSTREAM PROTEIN GLYCOREMODELING

CROSS-REFERENCE TO RELATED APPLICATIONS

This non-provisional Patent Application claims priority to U.S. Provisional Patent Application Ser. No. 61/917,793, filed Dec. 18, 2013, entitled "Method for in Vivo Production of Deglycosylated Recombinant Proteins Used as Substrate for Downstream Protein Glycoremodeling" the contents of which is incorporated by reference herein in its entirety.

TECHNICAL FIELD OF THE INVENTION

The present invention relates in general to the field of post-translational protein modifications, and more particularly, to methods of making proteins with reduced glycosylation in vivo.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with protein glycosylation.

The nature of N-glycosylation attached to therapeutic proteins is a critical attribute of the protein identity as it can affect its therapeutic activity, stability and immunogenicity properties. The N-glycan profile of recombinant proteins depends on the host used for its production and the host culture conditions. There is an increasing demand for manufacturing processes leading to the production of homogeneous and consistent therapeutic glycoproteins, composed ideally of one single optimal glycoform. For instance, afucosylated monoclonal antibodies have increased cytotoxicity activity. Also, human serum proteins used as therapeutics often require human-specific sialylation, which remains a challenge to uniformly produce in heterologous expression systems.

An in vitro therapeutics glyco-remodeling technology has been proposed by others to meet the demand of glycoengineered therapeutics (Huang, W., Giddens, J., Fan, S., Toonstra, C., & Wang, L. (2012). Chemoenzymatic glycoengineering of intact IgG antibodies for gain of functions. Journal of the American Chemical Society, 134, 12308-12318; and Wang, L., & Lomino, J. V. (2012). Emerging technologies for making glycan-defined glycoproteins. ACS chemical biology, 7(1), 110-22). The methods taught require the extraction and purification of the glycoprotein of interest, the deglycosylation of the protein, in such manner that the first N-acetylglucosamine (GlcNAc) and fucose, if attached remain attached to the asparagine residue of the protein, and the reglycosylation of the protein with a purified or synthesized activated N-glycan donor of choice using a proprietary endoglycosidase S (EndoS) mutant. The deglycosylation and reglycosylation steps are preceded and followed by purification steps that render the glycoremodeling process laborious and costly (See FIG. 1, Option A, and FIG. 2A, labeled as prior art).

Glycoremodeling methods are taught in, e.g., U.S. Pat. Nos. 8,361,961; 7,956,032; 7,696,163; and 7,338,933, issued to DeFrees, et al., include methods and compositions for remodeling a peptide molecule, including the addition or deletion of one or more glycosyl groups to a peptide, and/or the addition of a modifying group to a peptide, O-linked glycosylation of peptides, and glycopegylation of proteins.

Another method is taught in United States Patent Application No. 20130137857, filed by Wang, et al., entitled, Transglycosylation Activity Of Glycosynthase Mutants Of An Endo-Beta-N-Acetylglucosaminidase (Endo-D) From *Streptococcus Pneumoniae*. Briefly, the invention is said to include recombinant Endo-D and selected mutants that exhibit reduced hydrolysis activity and increased transglycosylation activity for the synthesis of glycoproteins wherein a desired sugar chain is added to a core fucosylated or nonfucosylated GlcNAc-protein acceptor by transglycosylation. Such recombinant Endo-D and selected mutants are said to be useful for efficient glycosylation remodeling of IgG1-Fc domain.

Yet another method is taught in United States Patent Application No. 20100173323, filed by Strome, et al., entitled Glycosylation Engineered Antibody Therapy. Briefly, this application is said to teach methods of generating a glycosylation-engineered antibody, and using the glycosylation-engineered antibody for treating a patient, particularly a cancer patient or a patient with an immune disease or disorder. The invention also includes methods of generating a glycosylation-engineered antibody for use in the treatment of patients having a polymorphism that does not respond to conventional antibody therapy, methods of improving the biological activity of an antibody by glycosylation engineering, and methods of modulating antibody-dependent cell-mediated cytoxicity (ADCC) using a glycosylation-engineered antibody.

SUMMARY OF THE INVENTION

In one embodiment, the present invention includes a method of reducing the glycosylation of proteins comprising: obtaining a cell that expresses one or more proteins that comprise one or more glycosylation sites and are glycosylated; expressing in the cell one or more glycosidases that cleave one or more glycosyl groups from the one or more proteins to reduce the glycosylation of the protein, wherein the glycosidase; and isolating the one or more proteins with reduced glycosylation from the cell. In one aspect, at least one of the one or more proteins, or the one or more one or more glycosidases, are transiently expressed. In another aspect, the cell is a plant cell, an insect cell, yeast, or a mammalian cell. In another aspect, the one or more proteins is an antibody, an antibody fragment, a growth factor, a lymphokine, an enzyme, a receptor, a receptor binding protein, a nucleic acid binding protein, a structural protein, a pore, a channel, a kinase, a phosphatase, or a G-protein. In another aspect, the one or more glycosidases is modified recombinantly to further comprise a portion that targets the one or more glycosidases into a particular cellular compartment of protein processing that causes glycosylation of the protein. In another aspect, the one or more glycosidases is modified recombinantly with a sequence that targets the glycosidase into the endoplasmic reticulum, or into vesicles past the endoplasmic reticulum. In another aspect, the one or more glycosidases are selected from glucosides, xylanases, sialylases, lactases, amylases, chitinases, sucrases, maltases, neuraminidases, invertases, hyaluronidases and lysozymes. In another aspect, the one or more glycosidases are selected from at least one of Endoglycosidase (e.g. EndoA, EndoF1, EndoF2, EndoF3, EndoD, EndoH, EndoM, EndoS), α-N-Acetylgalactosaminidase, α1-2 Fucosidase, α1-2,3 Mannosidase, α1-3,6 Galactosidase, α2-3 Neuraminidase, β-N-Acetylhexosaminidasef, β-N-Acetylglucosaminidase, β1-3 Galactosidase, β1-4 Galactosidase, O-Glycosidase, Neuraminidase, PNGase F, PNGase A, Fetuin, O-Glycosidase, Neuromimidase, β1-4 Galactosidase, or β-N-Acetylglucosaminidase. In another aspect, the method further comprises the step of adding new glycosylation to the one or more proteins after isolation in vitro or in vivo. In another aspect, the cell constitutively expresses the one or more proteins, the one or more glycosidases, or both.

In another embodiment, the present invention includes a method of reducing the glycosylation of proteins comprising: co-expressing one or more proteins that comprise one or more glycosylation sites and are glycosylated in a cell with one or more glycosidases, wherein the one or more glycosidases act to reduce or eliminate the glycosylation of the one or more proteins in the cell; and purifying the one or more proteins from the cell, wherein the glycosidase acts on glycosylation on the one or more proteins. In another aspect, at least one of the one or more proteins, or the one or more one or more glycosidases, are transiently expressed. In another aspect, the cell is a plant cell, an insect cell, a yeast, or a mammalian cell. In another aspect, the protein of interest is an antibody, an antibody fragment, a growth factor, a lymphokine, an enzyme, a receptor, a receptor binding protein, a nucleic acid binding protein, a structural protein, a pore, a channel, a kinase, a phosphatase, or a G-protein. In another aspect, the one or more glycosidases is modified recombinantly to further comprise a portion that targets the one or more glycosidases into a particular cellular compartment of protein processing that causes glycosylation of the protein. In another aspect, the one or more glycosidases is modified recombinantly with a sequence that targets the glycosidase into the endoplasmic reticulum, or into vesicles past the endoplasmic reticulum. In another aspect, the one or more glycosidases are selected from glucosides, xylanases, lactases, amylases, chitinases, sucrases, maltases, neuraminidases, invertases, hyaluronidases and lysozymes. In another aspect, the one or more glycosidases are selected from at least one of Endoglycosidase (e.g. EndoA, EndoF1, EndoF2, EndoF3, EndoD, EndoH, EndoM, EndoS), α-N-Acetylgalactosaminidase, α1-2 Fucosidase, α1-2,3 Mannosidase, α1-3,6 Galactosidase, α2-3 Neuraminidase, β-N-Acetylhexosaminidasef, β-N-Acetylglucosaminidase, β1-3 Galactosidase, β1-4 Galactosidase, O-Glycosidase, Neuraminidase, PNGase F, PNGase A, Fetuin, O-Glycosidase, Neuromimidase, β1-4 Galactosidase, or β-N-Acetylglucosaminidase. In another aspect, the method further comprises the step of adding new glycosylation to the one or more proteins after purification in vitro or in vivo. In another aspect, the method further comprises the step of adding new glycosylation to the one or more proteins after purification which are mutants of Endo H, α-N-Acetylgalactosaminidase, α1-2 Fucosidase, α1-2,3 Mannosidase, α1-3,6 Galactosidase, α2-3 Neuraminidase, β-N-Acetylhexosaminidasef, β-N-Acetylglucosaminidase, β1-3 Galactosidase, β1-4 Galactosidase, O-Glycosidase, Neuraminidase, PNGase F, Fetuin, O-Glycosidase, Neuromimidase, β1-4 Galactosidase, or β-N-Acetylglucosaminidase and that have glycosynthase activity. In another aspect, the cell constitutively expresses the one or more proteins, the one or more glycosidases, or both.

In one embodiment, the present invention includes a method of reducing the glycosylation of proteins comprising: co-expressing one or more proteins that comprise one or more glycosylation sites and are glycosylated and one or more glycosidases that cleaves one or more glycosylations from the one or more proteins in a cell; and purifying the one or more proteins from the cell, wherein the glycosidase acts on glycosylation on the one or more proteins; and reglycosylating the one or more proteins using a mutant glycosidase. In one embodiment, the present invention includes a method of evaluating a candidate drug believed to be useful in treating a disease state, the method comprising: a) measuring the level of the disease state from one or more tissues obtained from a set of patients suspected of having the disease state; b) administering a candidate protein that has been modified as described hereinabove to a first subset of the patients, and a comparison protein that has not been modified to a second subset of the patients; c) repeating step a) after the administration of the candidate drug or the comparison protein; and d) determining if the candidate drug has an improved medical outcome for the disease that is statistically significant or equivalent in the first subset of patients as compared to any reduction or equivalence occurring in the second subset of patients, wherein a statistically significant reduction or equivalence indicates that the candidate drug is useful in treating the disease state. In one aspect, the one or more proteins are selected from an antibody, an antibody fragment, a growth factor, a lymphokine, an enzyme, a receptor, a receptor binding protein, a nucleic acid binding protein, a structural protein, a pore, a channel, a kinase, a phosphatase, or a G-protein.

In one embodiment, the present invention includes a glycoprotein made by a method comprising: obtaining a cell that expresses one or more proteins that comprise one or more glycosylation sites and are glycosylated; expressing in the cell one or more glycosidases that cleaves one or more glycosyl groups from the one or more proteins to reduce the glycosylation of the protein; and isolating the one or more proteins from the cell, wherein the glycosidase acts on glycosylation on the one or more proteins in the cell to reduce the glycosylation of the one or more proteins. In another aspect, at least one of the one or more proteins, or the one or more one or more glycosidases, are transiently expressed. In another aspect, the cell is a plant cell, an insect cell, a yeast, or a mammalian cell. In another aspect, the one or more proteins is an antibody, an antibody fragment, a growth factor, a lymphokine, an enzyme, a receptor, a receptor binding protein, a nucleic acid binding protein, a structural protein, a pore, a channel, a kinase, a phosphatase, or a G-protein. In another aspect, the one or more glycosidases is modified recombinantly to further comprise a portion that targets the one or more glycosidases into a particular cellular compartment of protein processing that causes glycosylation of the protein. In another aspect, the one or more glycosidases is modified recombinantly with a sequence that targets the glycosidase into the endoplasmic reticulum, or into vesicles past the endoplasmic reticulum. In another aspect, the one or more glycosidases are selected from glucosides, xylanases, lactases, amylases, chitinases, sucrases, maltases, neuraminidases, invertases, hyaluronidases and lysozymes. In another aspect, the one or more glycosidases are selected from at least one of Endoglycosidase (e.g. EndoA, EndoF1, EndoF2, EndoF3, EndoD, EndoH, EndoM, EndoS), α-N-Acetylgalactosaminidase, α1-2 Fucosidase, α1-2,3 Mannosidase, α1-3,6 Galactosidase, α2-3 Neuraminidase, β-N-Acetylhexosaminidasef, β-N-Acetylglucosaminidase, β1-3 Galactosidase, β1-4 Galactosidase, O-Glycosidase, Neuraminidase, PNGase F, PNGase A, Fetuin, O-Glycosidase, Neuromimidase, β1-4 Galactosidase, or β-N-Acetylglucosaminidase. In another aspect, the glycoprotein further comprises the addition of a new glycosylation to the one or more proteins after isolation. In another aspect, the cell constitutively expresses the one or more proteins, the one or more glycosidases, or both.

In one embodiment, the present invention includes a glycoprotein made by a method comprising: expressing a protein in a plant cell that is recombinantly modified to expresses a glycosidase; isolating the protein expressed and deglycosylated in the cell; re-glycosylating the protein in the presence of one or more saccharides in at least one of in vitro or in cellulo; and isolating the glycosylated protein.

BRIEF DESCRIPTION OF THE DRAWINGS

For a more complete understanding of the features and advantages of the present invention, reference is now made to the detailed description of the invention along with the accompanying figures and in which:

FIG. 1, Option A, shows the prior art used by others. FIG. 1, Option B, shows the pathway of the present invention involving the in vivo deglycosylation of the protein of interest (e.g. rituximab). In FIG. 1, Option B, high-mannose glycans attached to the protein of interest are cleaved off, leaving a deglycosylated substrate for in vitro reglycosylation.

DETAILED DESCRIPTION OF THE INVENTION

Figure 1:
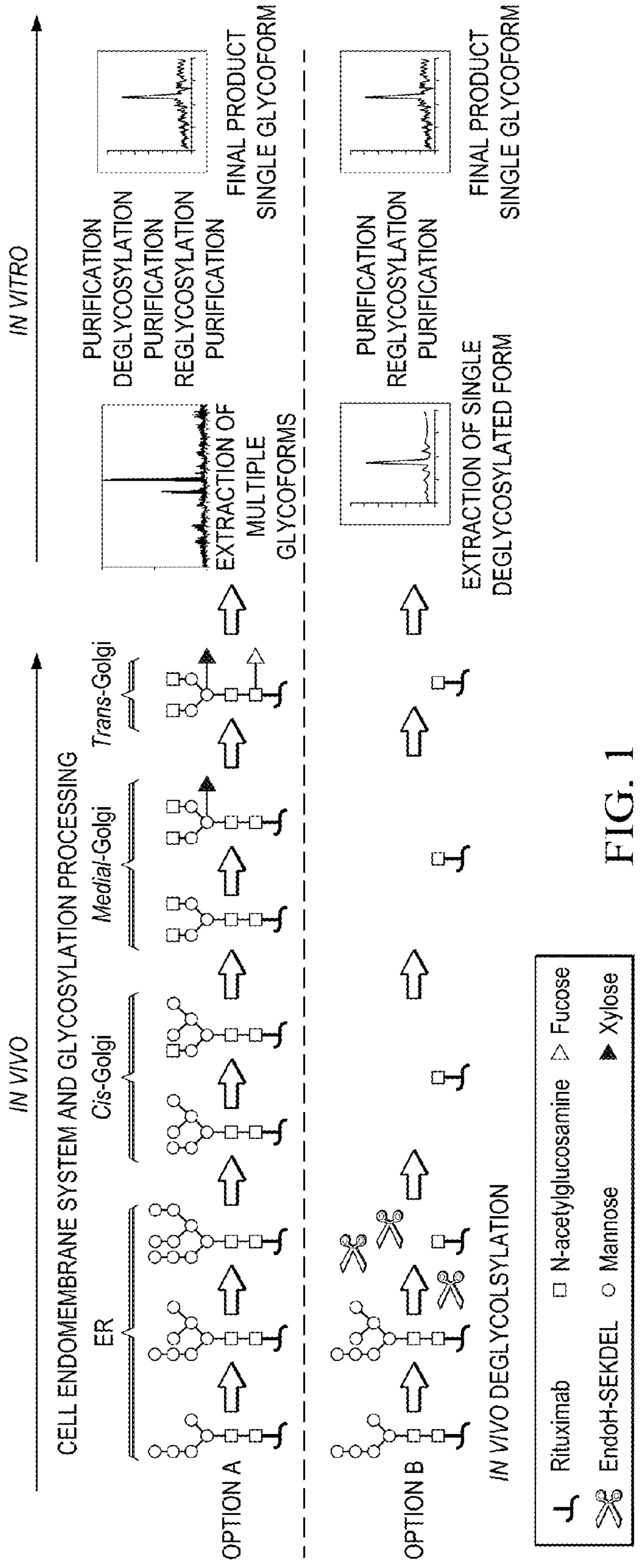
FIG. 1, OPTION A and FIG. 1, OPTION B show in vivo and in vitro N-glycan processing of recombinant proteins, respectively under a glycoremodeling strategy.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as “a”, “an” and “the” are not intended to refer to only a singular entity, but include the general class of which a specific example may be used for illustration. The terminology herein is used to describe specific embodiments of the invention, but their usage does not delimit the invention, except as outlined in the claims.

As used herein, the terms “carbohydrate,” polysaccharide,” or “sugar” are used interchangeably to refer to a monosaccharide, disaccharide, trisaccharide, oligosaccharide, or polysaccharide, including but not limited to, e.g., mannose, galactose, N-acetylglucosamine, N-acetylneuraminic acid (sialic acid), glucose, fructose, fucose, sorbose, rhamnose, mannoheptulose, N-acetylgalactosamine, dihydroxyacetone, xylose, xylulose, arabinose, glyceraldehyde, sucrose, lactose, maltose, trehalose, cellobiose or any combination thereof of the L- or D-isomer, whether oxidized or not. The terms “carbohydrate,” polysaccharide,” “sugar” includes molecules produced naturally, recombinantly, synthetically, and/or semi-synthetically, which may be linear and/or branched.

One or more of the standard techniques are used for recombinant DNA, oligonucleotide synthesis, and tissue culture and transformation (e.g. electroporation, lipofection), as will be well-known to those of skill in the art. For example, enzymatic reactions and purification techniques are performed according to manufacturer’s specifications or as commonly accomplished in the art or as described herein. The foregoing techniques and procedures are as generally performed according to conventional methods well known in the art and as described in various general and more specific references that are cited and discussed throughout the present specification. See Sambrook et al., Molecular Cloning: A Laboratory Manual, 2d ed., Cold Spring Harbor Laboratory Press, Cold Spring Harbor, N.Y. (1989), Ausubel et al., Current Protocols in Molecular Biology, Greene Publishing Associates (1992), and Harlow and Lane, Antibodies: A Laboratory Manual, Cold Spring Harbor Laboratory Press, Cold Spring Harbor, N.Y. (1990), which are incorporated herein by reference in their entirety for all purposes. The nomenclatures used in connection with, and the laboratory procedures and techniques of, analytical chemistry, synthetic organic chemistry, and medicinal and pharmaceutical chemistry described herein are those well known and commonly used in the art.

Techniques and compositions for making useful dosage forms using the present invention are described in one or more of the following references: Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; *Remington's Pharmaceutical Sciences,* 20th Ed., Lippincott Williams & Wilkins., 2000; Martindale, The Extra Pharmacopoeia, Thirty-Second Edition (The Pharmaceutical Press, London, 1999); all of which are incorporated by reference, and the like, relevant portions incorporated herein by reference.

As used herein, the term "gene" referred to a functional protein, polypeptide or peptide-encoding unit. As will be understood by those in the art, this functional term includes genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated.

As used herein, the term "vector" is used in reference to nucleic acid molecules that transfer DNA segment(s) from one cell to another. The vector may be further defined as one designed to propagate specific sequences, or as an expression cassette that includes a promoter operatively linked to the specific sequence, or one designed to cause such a promoter to be introduced. The vector may exist in a state independent of the host cell chromosome, or may be integrated into the host cell chromosome.

As used herein, the term "host cell" refers to cells that have been engineered or manipulated to contain nucleic acid segments or altered segments, whether archeal, prokaryotic, or eukaryotic. Thus, engineered, or recombinant cells, are distinguishable from naturally occurring cells that do not contain recombinantly introduced genes through the hand of man. Non-limiting examples of manipulations include transgenic, stable transfection, or transient transfections.

As used herein, the term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

As used herein, the term "antibody" refers to an intact immunoglobulin of any isotype, or a fragment thereof, that can compete with the intact antibody for specific binding to the target antigen, and includes chimeric, humanized, fully human, and bispecific antibodies. An intact antibody generally will comprise at least two full-length heavy chains and two full-length light chains, but in some instances may include fewer chains made recombinantly or found naturally. Antibodies may be derived solely from a single source, or may be "chimeric," that is, different portions of the antibody may be derived from two different antibodies. For example, the complementarity determining region (CDR) may be derived from a rat, mouse, or hamster source, while the framework region of the V region is derived from a different animal source, e.g., a human. The antibodies or binding fragments may be produced in hybridomas, by recombinant DNA techniques, using phase-display, or by enzymatic or chemical cleavage of intact antibodies. Unless otherwise indicated, the term "antibody" includes, in addition to antibodies comprising two full-length heavy chains and two full-length light chains, derivatives, variants, fusion proteins, fragments, and mutants thereof.

As used herein, the term "light chain" refers to a full-length light chain and fragments thereof having sufficient variable region sequence to confer binding specificity. A full-length light chain includes a variable region domain (abbreviated herein as $V_L$), and a constant region domain (abbreviated herein as $C_L$). The variable region domain of the light chain is at the amino-terminus of the polypeptide. The light chains include kappa chains and lambda chains.

As used herein, the term "heavy chain" refers to a full-length heavy chain and fragments thereof having sufficient variable region sequence to confer binding specificity. A full-length heavy chain includes a variable region domain (abbreviated herein as $V_H$), and three constant region domains (abbreviated herein as $C_{H1}$, $C_{H2}$, and $C_{H3}$). The $V_H$ domain is at the amino-terminus of the polypeptide, and the $C_H$ domains are at the carboxy-terminus, with the $C_{H3}$ being closest to the —COOH end. Heavy chains may be of any isotype, including IgG (including $IgG_1$, $IgG_2$, $IgG_3$, and $IgG_4$ subtypes), IgA (including $IgA_1$ and $IgA_2$ subtypes), IgM, and IgE, or equivalents thereof in other animals.

As used herein, the term "Fab'" refers to a polypeptide comprising a heterodimer of the variable domain and the first constant domain of an antibody heavy chain, plus the variable domain and constant domain of an antibody light chain, plus at least one additional amino acid residue at the carboxy terminus of the heavy chain $C_H1$ domain including one or more cysteine residues. $F(ab')_2$ antibody fragments are pairs of Fab' antibody fragments which are linked by a covalent bond(s). The Fab' heavy chain may include a hinge region. This may be any desired hinge amino acid sequence. Alternatively the hinge may be entirely omitted in favor of a single cysteine residue or, a short (about 1-10 residues) cysteine-containing polypeptide. In certain applications, a common naturally occurring antibody hinge sequence (cysteine followed by two prolines and then another cysteine) is used; this sequence is found in the hinge of human $IgG_1$ molecules (E. A. Kabat, et al., Sequences of Proteins of Immunological Interest 3rd edition (National Institutes of Health, Bethesda, Md., 1987)). In other embodiments, the hinge region is selected from another desired antibody class or isotype. In certain preferred embodiments of this invention, the C-terminus of the $C_H1$ of Fab' is fused to the sequence Cys X X. X can be Ala, although it may be any other residue such as Arg, Asp, or Pro. One or both X amino acid residues may be deleted.

As used herein, the term "hinge region" refers to an amino acid sequence located between $C_H1$ and $C_H2$ in native immunoglobulins or any sequence variant thereof. Analogous regions of other immunoglobulins will be employed, although it will be understood that the size and sequence of the hinge region may vary widely. For example, the hinge region of a human $IgG_1$ is only about 10 residues, whereas that of human $IgG_3$ is about 60 residues.

As used herein, the term "Fv" refers to a covalently or noncovalently-associated heavy and light chain heterodimer which does not contain constant domains.

As used herein, the term "Fv-SH" or "Fab'-SH" are defined herein as a Fv or Fab' polypeptide having a cysteinyl free thiol. The free thiol is in the hinge region, with the light and heavy chain cysteine residues that ordinarily participate in inter-chain bonding being present in their native form. In the most preferred embodiments of this invention, the Fab'-SH polypeptide composition is free of heterogenous proteolytic degradation fragments and is substantially (greater than about 90 mole percent) free of Fab' fragments wherein heavy and light chains have been reduced or otherwise derivatized so as not to be present in their native state, e.g. by the formation of aberrant disulfides or sulfhydryl addition products.

As used herein, the terms "glycosidase" "glycoside hydrolase" or "glycosyl hydrolase" refers to enzymes that assist in the hydrolysis of glycosidic bonds in complex sugars, e.g., polysaccharides. In certain non-limiting examples of the present invention the polysaccharides are attached to a glycoprotein, that is, a protein or polypeptide to which one or more polysaccharide chains are attached. Non-limiting examples of glycosidases for use with the present invention include Endoglycosidase (e.g. EndoA, EndoF1, EndoF2, EndoF3, EndoD, EndoH, EndoM, EndoS), α-N-Acetylgalactosaminidase, α1-2 Fucosidase, α1-2,3 Mannosidase, α1-3,6 Galactosidase, α2-3 Neuraminidase, β-N-Acetylhexosaminidasef, β-N-Acetylglucosaminidase, β1-3 Galactosidase, β1-4 Galactosidase, O-Glycosidase, Neuraminidase, PNGase F, PNGase A, Fetuin, O-Glycosidase, Neuromimidase, β1-4 Galactosidase, and/or β-N-Acetylglucosaminidase.

As used herein, the term "glycosylation" refers to the addition of saccharides or glycosyl groups to a polypeptide, which is typically either N-linked or O-linked. N-linked glycosylation refers to the attachment of the carbohydrate moiety to the side chain of an asparagine residue. Non-limiting examples of the tri-peptide sequences includes asparagine-X-serine and asparagine-X-threonine, where X is any amino acid except proline, which are the typical recognition sequences for enzymatic attachment of the carbohydrate moiety to the asparagine side chain. The presence of these tri-peptide sequences in a polypeptide creates a potential glycosylation site. O-linked glycosylation refers to the attachment of one of the sugars (e.g., N-acetylgalactosamine, galactose, or xylose), to a hydroxyamino acid, most commonly serine or threonine, although 5-hydroxyproline or 5-hydroxylysine may also be used. For use with the present invention, the re-glycosylation of a protein can be in vitro and/or in cellulo.

As used herein, the term "humanized antibody" refers to an immunoglobulin amino acid sequence variant or fragment thereof that is capable of binding to a predetermined antigen and that includes an FR region having substantially the amino acid sequence of a human immunoglobulin and a CDR having substantially the amino acid sequence of a non-human immunoglobulin or a sequence engineered to bind to a preselected antigen.

As used herein, the terms "cell" and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

As used herein, the term "plasmids" referred to with a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

As used herein, the terms "recovery" or "isolation" of a given fragment of DNA from a restriction digest refers to the separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (Nucleic Acids Res. 1981. 9:6103-6114), and Goeddel et al. (Nucleic Acids Res. 1980. 8:4057).

As used herein, the term "preparation" of DNA refers to the isolation of plasmid DNA from a culture of the host cells. Methods used commonly for DNA preparation are the large and small-scale plasmid preparations described in sections 1.25-1.33 of Sambrook et al., (Molecular Cloning: A Laboratory Manual New York: Cold Spring Harbor Laboratory Press, 1989). DNA preparations are purified by methods well known in the art (see section 1.40 of Sambrook et al., supra).

As used herein, the term "transformation," refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome.

As used herein, the term "transfection" refers to the introduction of foreign DNA into eukaryotic cells. Transfection may be accomplished by a variety of methods known to the art including, e.g., calcium phosphate-DNA co-precipitation, DEAE-dextran-mediated transfection, polybrene-mediated transfection, *agrobacteria*-mediated transfection, electroporation, microinjection, liposome fusion, lipofection, protoplast fusion, retroviral infection, and biolistics. Thus, the term "stable transfection" or "stably transfected" refers to the introduction and integration of foreign DNA into the genome of the transfected cell. The term "stable transfectant" refers to a cell that has stably integrated foreign DNA into the genomic DNA. The term also encompasses cells that transiently express the inserted DNA or RNA for limited periods of time. Thus, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "vector" refers to nucleic acid molecules that transfer DNA segment(s) from one cell to another. The term "vehicle" is sometimes used interchangeably with "vector." The term "vector" as used herein also includes expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The present invention also includes the modification of protein sequences to alter, delete, and/or add, glycosylation or carbohydrate attachment sites. For example, protein variants can also be produced that have a modified glycosylation pattern relative to the parent protein, for example, deleting one or more carbohydrate moieties found in the specific binding agent or antibody, and/or adding one or more glycosylation sites that are not present in the specific binding agent or antibody.

Glycosylation of proteins (e.g., antibodies) will typically include at least one of N-linked or O-linked carbohydrate groups. As used herein, "N-linked" glycosylation refers to the attachment of a carbohydrate moiety to the side chain of an asparagine residue. For example, the tri-peptide sequences asparagine-Xaa-threonine or asparagine-Xaa-serine, where Xaa is any amino acid except proline, are typical recognition sequences for enzymatic attachment of the carbohydrate moiety to the asparagine side chain. The presence of either of these tripeptide sequences in a polypeptide creates a potential glycosylation site. As such, N-linked glycosylation sites may be added to a protein by altering the amino acid sequence to include one or more of these tri-peptide sequences. As used herein, "O-linked" glycosylation refers to the attachment of carbohydrate groups (e.g., N-acetylgalactosamine, galactose, or xylose to a hydroxyamino acid), to a serine, threonine, hydroxyproline, or hydroxylysine.

The present invention overcomes the problems with existing in vitro glycoremodeling by shortening the process (and potentially increasing the product yield), ultimately reducing the cost and time of a glycoremodeling process, and making it more amenable for large-scale manufacturing. The deglycosylation step is conducted in vivo by co-expressing the protein(s) of interest with a specific endoglycosidase. Endoglycosidases cleave N-glycan substrates attached to proteins after the first GlcNAc residue producing a deglycosylated protein available for reglycosylation (present invention, FIG. 1, Option B). The choice of the endoglycosidase will depend upon the cell compartment where the protein of interest accumulates and the nature of the N-glycan substrate to cleave off. For example, a specific endoglycosidase (e.g. EndoH) can be targeted to the endoplasmic reticulum (ER) to cleave high-mannose residues attached to the protein of interest before fucosylation of the N-glycan core occurs (FIG. 1, Option B). Upon extraction of the protein of interest from the expressing tissue or culture, the deglycosylated protein will be purified and subjected to an in vitro reglycosylation step.

Figure 2A:
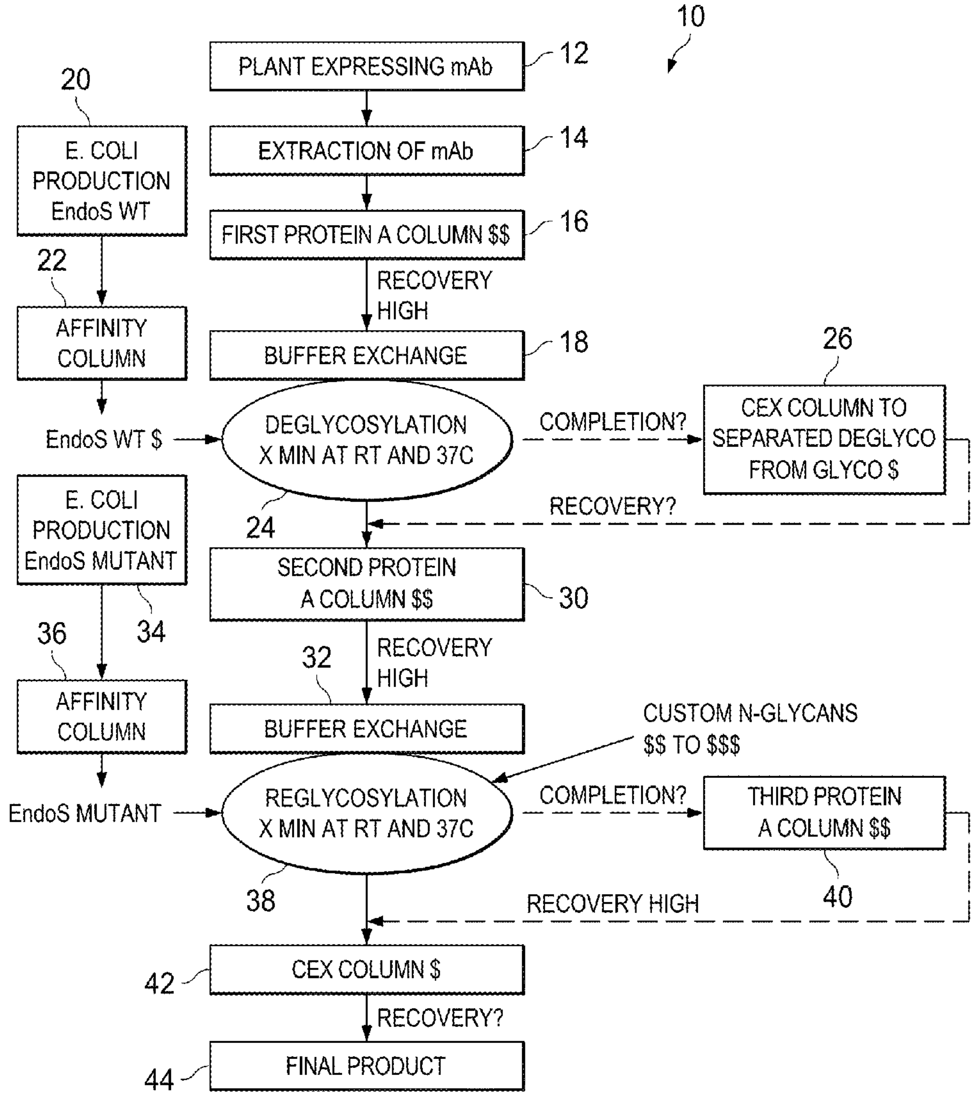
FIG. 2A shows a schematic representation of monoclonal antibody glycoremodeling of the prior art, which uses an in vitro process for deglycosylation and reglycosylation. In contrast.

FIG. 2A shows a schematic representation of monoclonal antibody glycoremodeling of the prior art, which uses an in vitro process for deglycosylation and reglycosylation. The prior art process 10, begins with the expression of a monoclonal antibody (mAb) in a plant at step 10, followed by extraction of the mAb at step 14. Next, in step 16 the mAb is applied to protein A column, and the binding buffer is exchanged one or more times at step 18. In parallel, an *E. coli* is used to produce wild-type (WT) EndoS at step 20, followed by affinity purification of the same at step 22. The EndoS obtained from the affinity purification is then added at step 24 to the protein isolated at step 18, and the mAb is deglycosylated for a certain amount of time at certain temperatures. Next, the mAb is again purified at step 30 using a second protein A column, again followed by a buffer exchange step 32. In parallel, a mutant EndoS is produced in *E. coli* at step 34, and affinity purified at step 36 to produce mutant EndoS. The mutant EndoS produced thereby is then combined with the deglycosylated mAb from step 32 in step 38. As this stage, the reglycosylated mAb can then be reisolated on a third protein A column at step 40, or the mAb can be affinity purified using a CEX column at step 42, followed by isolation of the final product at step 44.

Figure 2B:
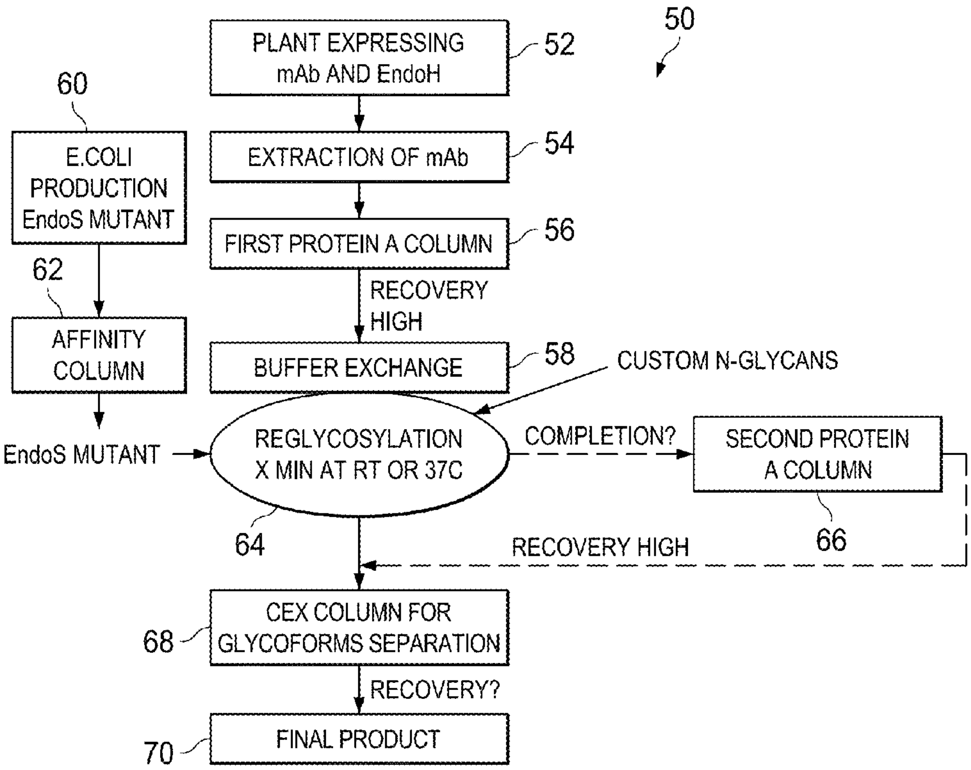
FIG. 2B shows a schematic representation of monoclonal antibody glycoremodeling of the present invention using in vivo deglycosylation followed by in vitro reglycosylation.

In contrast, FIG. 2B shows a schematic representation of monoclonal antibody glycoremodeling of the present invention using in vivo deglycosylation followed by in vitro reglycosylation. The process of the present invention 50, begins with the co-expression of the protein of interest, e.g., a mAb, with an enzyme that deglycosylates the protein of interest in vivo at step 52. Next, at step 54 the protein of interest is extracted and in step 56 is isolated using, e.g., an affinity column, which can then be washed via buffer exchange at step 58. In parallel, an *E. coli* is used to express a mutant glycosidase, e.g., an EndoS mutant at step 60, followed by isolation of the EndoS mutant at step 62. In step 64, the isolated deglycosylated protein of interest is combined with the mutant glycosidase to reglycosylate the protein of interest. The reglycosylated protein of interest can then be further isolated using a second protein A column at step 66, or can be affinity isolated using, e.g., a CEX column can be used to isolate different glycoforms at step 68, followed by the isolation of the final product at step 70.

Construction of Plant Vector System. The genetic sequence of rituximab heavy and light chains (GenBank: AX556949.1), a human IgG1, Classical Swine Fever Virus (CSFV) E2 coat protein (GenBank: ACL98470.1), and Endoglycosidase H (GenBank: AAA26738.1) were fused to the barley α-amylase signal peptide sequence (GenBank: CAX51374.1). The sequence corresponding to the transmembrane domain of the CSFV E2 protein was removed to generate a gene encoding for a soluble CSFV E2 protein. The recombinant CSFV E2 sequence was also fused to a 6× histidine tag to facilitate purification and the endoplasmic reticulum (ER) retrieval HDEL tag to allow accumulation of the protein in the endoplasmic reticulum. All genes were codon optimized for plant expression using the *Nicotiana tabaccum* codon usage table and synthesized by Eurofins MWG/Operon (Huntsville, Ala.). Codon usage optimization is well-known in the art, e.g., using the tables taught by Christianson, M., Codon usage patterns distort phylogenies from or of DNA sequences, Am. J. Bot. August 2005, Vol. 92, No. 8, pp. 1221-1233, Puigbo, et al., OPTIMIZER: a web server for optimizing the codon usage of DNA sequences, Nucleic Acids Res. 2007 July; 35(Web Server issue): W126-W131, relevant tables incorporated herein by reference and freely available from, e.g., www.jcat.de or genomes.urv.es/OPTIMIZER. Rituximab, hIgG1 and E2 genes were cloned into a plant viral-based expression vector. The EndoH gene was first fused to the sequences of the ER-retrieval peptide SEKDEL (SEQ ID NO.: 1) and the 3× peptide Flag tag at the 3' end before being cloned into the binary vector pGREENII to produce pFlag-EndoH. The expression of the EndoH gene was driven by the duplicated CaMV 35S promoter. All plant expression vectors were then mobilized into *Agrobacteria tumefaciens* strain GV3101.

Plant growth. *N. benthamiana* seeds were germinated under constant proprietary red/blue LED light for three weeks at ~25° C. with relative humidity of ~60%. For the first two weeks light intensity was between 30-50 μmol/$m^2$/s, and for the third week light intensity was increased to 50-70 μmol/$m^2$/s. After three weeks, young plantlets were transferred to a new tray for another two weeks of growth expansion. For the first week of growth expansion, plants were placed at ~25° C. with relative humidity of ~65% and under a photoperiod of 16 h light (50-70 mmol/$m^2$/s)/8 h dark. For the second week of growth expansion, plants were placed at ~27° C. with relative humidity of ~45% and under constant light (70-130 μmol/$m^2$/s).

Agro-infiltration. *Agrobacteria* clones were grown individually in culture flasks containing Luria-Bertani (LB) medium supplemented with 50 mg/L kanamycin and 25 mg/L rifampicin at 28° C. with agitation of 225 rpm. Cultures reaching an $OD_{600\ nm}$ of ~1.5 were collected and diluted in infiltration solution containing 2 mM MES buffer pH 5.6. After one hour *Agrobacteria* induction time, 5 weeks old plants were vacuum infiltrated as described below. Plants were immersed in infiltration solution containing *Agrobacteria* and a vacuum of 23 inch Hg was applied and hold for 3 minutes. Agro-infiltrated plants were incubated in a new growth chamber under constant light (70-130 μmol/$m^2$/s) at ~22° C. with relative humidity of 50%.

Protein extraction and purification. After 6-7 days of growth post infiltration (DPI), plant leaves were harvested and total soluble protein were extracted in 3 volumes (w:v) of extraction buffer (50 mM sodium phosphate, pH 8.0) Sodium chloride (150 mM) and EDTA (5 mM) were supplemented to the extraction buffer for the recovery of rituximab and hIgG1. Extracts were spun down for 10 minutes to pellet plant tissue. The supernatant was recovered for purification and protein characterization. Expression of Flag-EndoH was confirmed by western blot analysis using an anti-Flag antibody (Rockland Antibodies and Assays, Gilbersville, Pa.). Plant made Rituximab and hIgG1 were purified from total soluble protein using the HiTrap MabSelect SuRe Column (GE Healthcare Life Sciences, Piscataway, N.J.). Protein E2 was purified by Immobilized Metal Ion Affinity Chromatography (IMAC) using Chelating Sepharose Fast-Flow charged with nickel (GE Healthcare Life Sciences, Piscataway, N.J.), following the manufacturer instructions.

Recombinant Protein Molecular Mass Determination.

Plant-made CSFV E2, plant-made and commercially available rituximab (Rituxan®) were analyzed by MALDI-TOF-MS (Applied Biosystems). Samples reduced in 5% β-mercaptoethanol were incubated for 20 minutes at 57° C. Reduction of the fully-assembled monoclonal antibody yielded free heavy chain and light chain for direct molecular weight determination. Samples were diluted 1:20 and/or 1:200 in a saturated solution of sinapinic acid (10.0 mg/mL: 75% ACN:25% $H_2O$) and 1 μL spots were applied to a 100-spot sample plate. Dried droplets were analyzed with optimized instrument parameters in the positive-ion mode.

Tryptic Peptide Mass Fingerprinting. Samples diluted to 1.0 mg/mL were incubated for 20 minutes at 57° C. in the presence of DTT. Following reduction, carbamidomethylation was performed by sample incubation with iodoacetamide in the dark for 20 minutes at room temperature. Digestion with trypsin, sequencing grade (Promega) was performed for 2 hours at 57° C. in the presence of 0.1% ProteaseMax surfactant (Promega). Peptides were purified by evaporating the samples to dryness under a gentle stream of nitrogen and resuspension in 65% ACN:0.1% TFA for a total of three times. Samples were resuspended in a volume of 0.1% TFA prior to diluting 1:20 and/or 1:200 in a saturated solution of α-cyano-4-hydroxycinnamic acid (10.0 mg/mL:75% ACN:25% $H_2O$) and 1 μL spots were applied to a 100-spot sample plate for MALDI-TOF-MS analysis. Dried droplets were analyzed with optimized instrument parameters in the positive-ion mode.

EXAMPLE 1

In Vivo Deglycosylation of a Monoclonal Antibody (Human IgG1)

Figure 3:
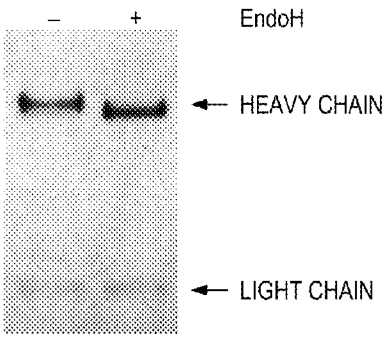
FIG. 3 shows a SDS-PAGE of pure hIgG1 originated from plant tissue expressing either hIgG1 alone (−) or together with EndoH (+). Note the shift in molecular weight of the antibody heavy chain when expressed with EndoH due to in planta deglycosylation.
Figure 4:
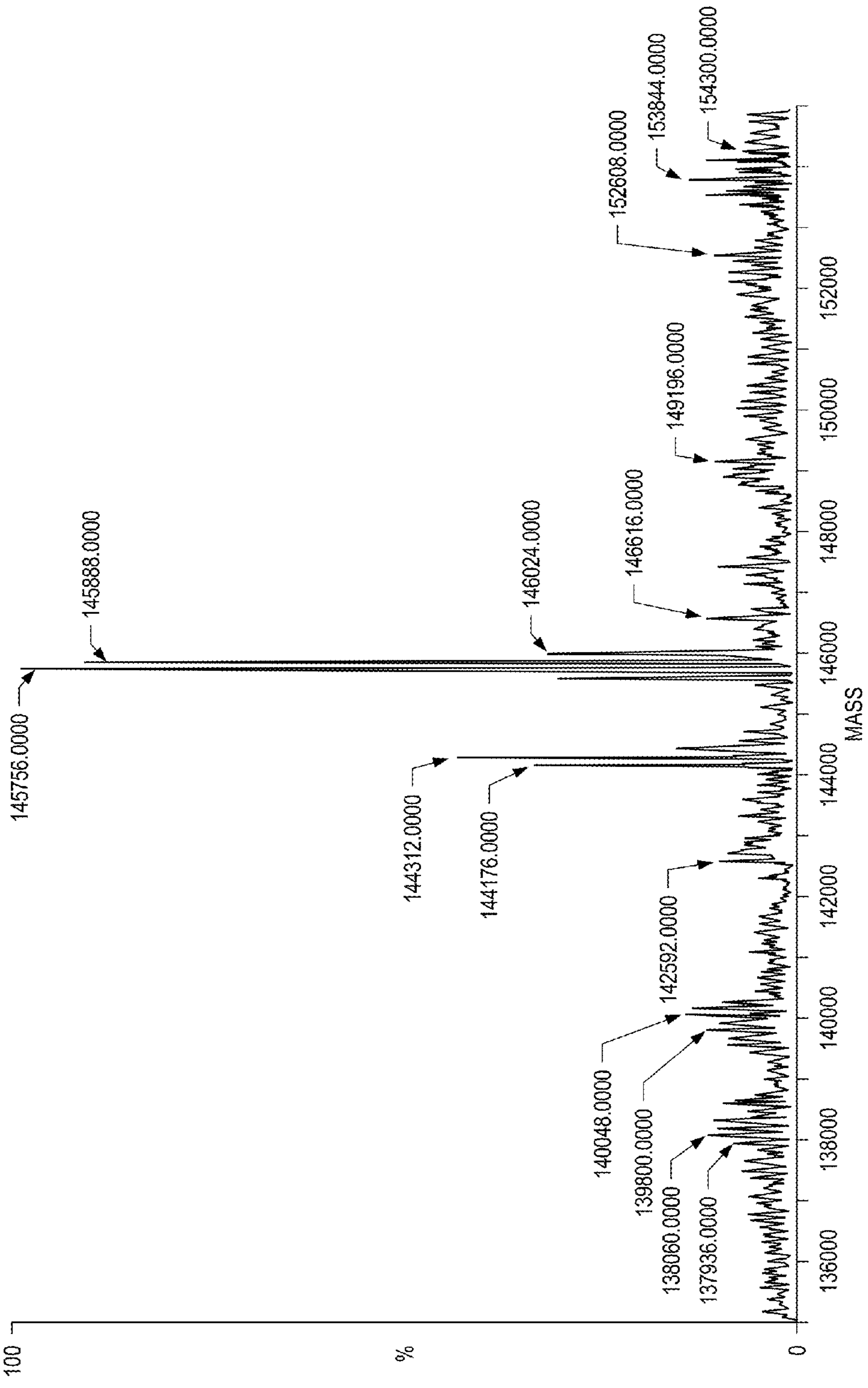
FIG. 4 shows a deconvoluted ESI-MS spectrum of hIgG1 obtained from plant tissue expressing hIgG1 alone. Samples were analyzed in non-reducing condition. The majority of the protein is glycosylated on both heavy chains with a minority of hIgG1 hemiglycosylated (with only one of the two heavy chains glycosylated).
Figure 5:
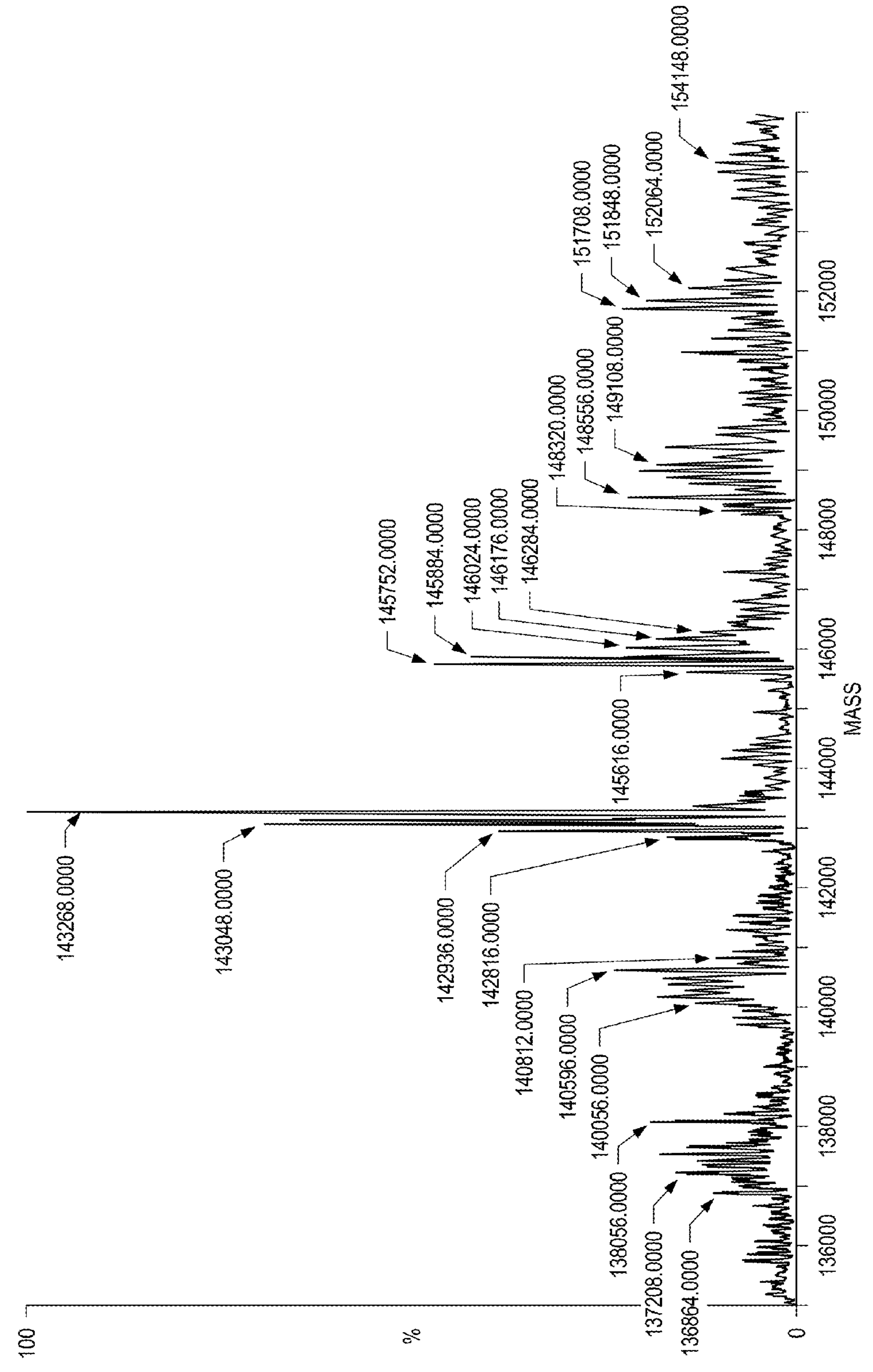
FIG. 5 shows a deconvoluted ESI-MS spectrum of hIgG1 obtained from plant tissue expressing hIgG1 with EndoH. Samples were analyzed in non-reducing condition. Note the shift in molecular weight from the glycosylated form to the deglycosylated form of the protein. The deglycosylated hIgG1, with a mass of 143,268 Da, corresponds to the theoretical mass of the protein with two N-acetylhexosamine (GlcNAc) attached on each heavy chain.

In Example 1, the inventors produced a human IgG1 (hIgG1) in *Nicotiana benthamiana* plants and remove in planta N-linked oligosaccharides after the first GlcNAc from the heavy chain with the ultimate goal of engineering an afucosylated and sialylated single glycoform antibody product. To reach this goal, we transiently expressed the light and heavy chain of the hIgG1 together with the endoglycosidase H fused to the endoplasmic reticulum retrieval signal SEKDEL (SEQ ID NO.: 1) using plant vacuum agroinfiltration. Endoglycosidase H (EndoH) specifically cleaves high-mannose glycans, which are glycoforms found in the ER of eukaryote cells (e.g. plants and mammalian cells). At this stage (protein localized in the ER) of plant N-glycosylation processing, the fucose residue has not been added to the N-glycan core of the protein yet. Therefore, the cleavage of high-mannose glycans will allow the production of deglycosylated and afucosylated hIgG1. Once plants transiently expressed hIgG1 with EndoH, total soluble proteins were extracted from expressing tissue and the hIgG1 was purified from crude extracts using a protein A column. The purified product either expressed with or without EndoH was loading on a protein gel in reduced condition where the size difference between the two heavy chains can be visualized indicating in planta deglycosylation of the protein when co-expressed with EndoH (FIG. 3). The glycosylation nature of the purified hIgG1 was further evaluated by Electrospray Ionization Mass Spectrometry (ESI-MS) in order to characterize fully glycosylated hIgG1 (FIG. 4) and deglycosylated hIgG1 (FIG. 5). The hIgG1 was expressed as a fully and hemi-glycosylated antibody in plants with a molecular mass of 145,756 Da and 144,312 Da respectively showing that in the hemi-glycosylated form, only one heavy chain is glycosylated (FIG. 4). The difference between the hemi-glycosylated and fully glycosylated protein is about 1,444 Da which is the average mass of one N-glycan. In contrast, when hIgG1 was co-expressed with EndoH in plants, the mass of the assembled antibody was reduced to ~143,048 Da and ~143,268 Da (FIG. 5), representing two antibodies with either one (hemi) or two (full) chains harboring a single N-acetylglucosamine (GlcNAc, mass of 203 Da), yet larger than the non-glycosylated hIgG1 with a mass of 142,928 Da.

EXAMPLE 2

In Vivo Deglycosylation of a Monoclonal Antibody (Rituximab)

In example 2, the inventors repeated the in vivo deglycosylation of another monoclonal antibody: the chimeric anti-CD20 antibody rituximab. Rituximab heavy and light chains were expressed in plant either alone or with EndoH. Once purified from plant total extracts, plant-made rituximab samples were analyzed by matrix-assisted laser desorption ionization time-of-flight mass spectrometry (MALDI-TOF MS) to determine if in planta deglycosylation by EndoH was consistent with the in vitro deglycosylation process where the anchored N-acetylglucosamine (GlcNAc) remained with the asparagine residue of the protein and/or tryptic peptide fragment. To confirm this process, both full-length and tryptic peptide MALDI-TOF spectra were acquired for (1) the innovator molecule (Rituxan®), (2) plant-made rituximab and (3) the plant-made rituximab that was deglycosylated in planta with EndoH.

Figure 6:
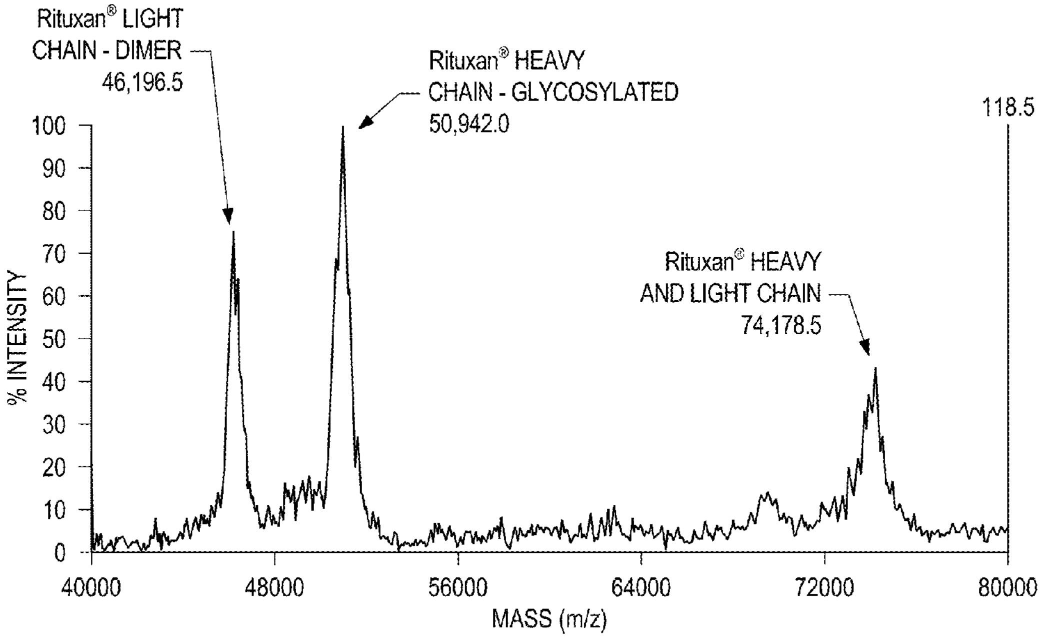
FIG. 6 shows the MALDI-TOF mass spectrum of Rituxan® standard following reduction with β-mercaptoethanol displaying m/z 40,000 to 80,000 mass range.
Figure 7:
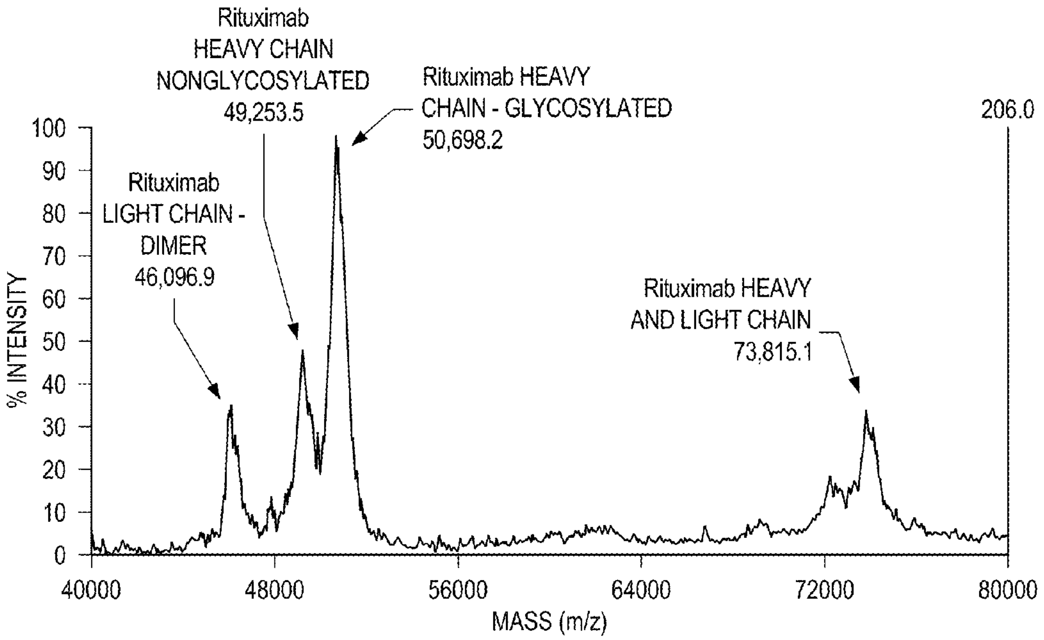
FIG. 7 shows a MALDI-TOF mass spectrum of plant-made rituximab following reduction with β-mercaptoethanol displaying m/z 40,000 to 80,000 mass range.
Figure 8:
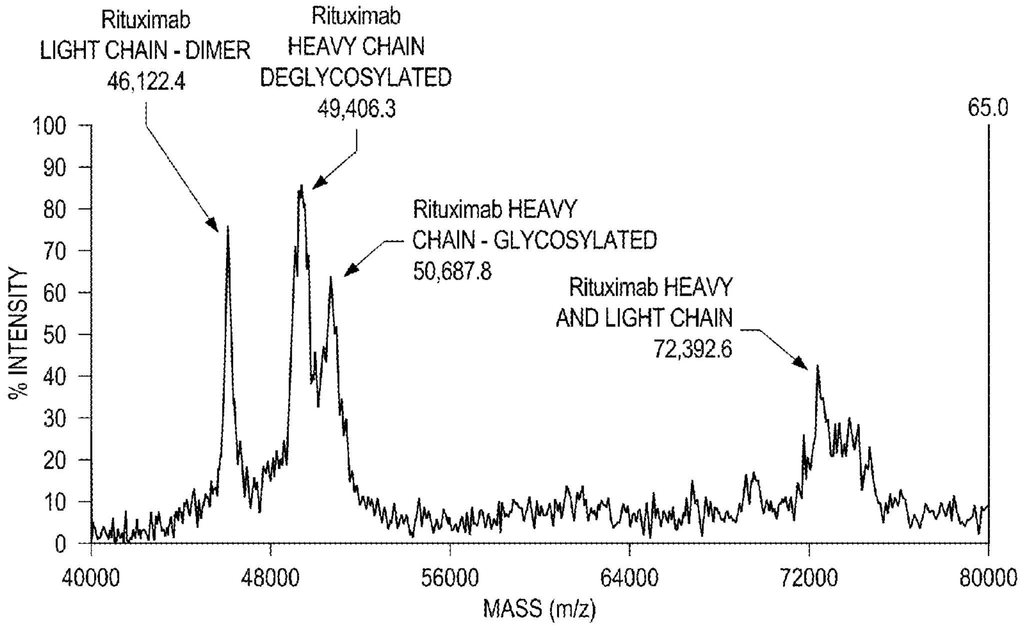
FIG. 8 shows a MALDI-TOF mass spectrum of plant-made rituximab deglycosylated in planta with EndoH and reduced with β-mercaptoethanol displaying m/z 40,000 to 80,000 mass range.
Figure 9:
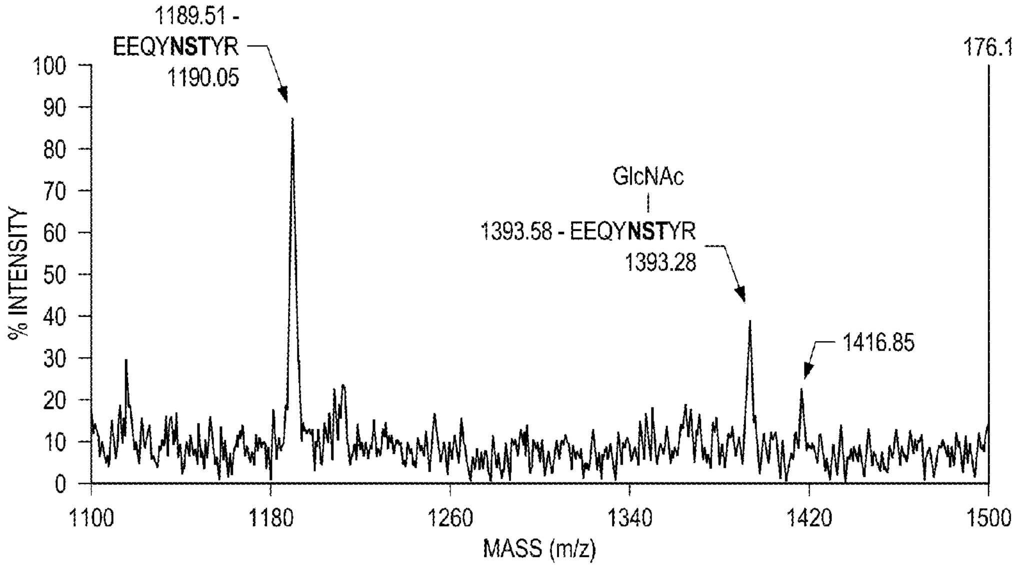
FIG. 9 shows a zoomed (m/z 1100-1500) MALDI-TOF mass spectrum of in planta EndoH deglycosylated rituximab followed by tryptic digestion.

FIG. 6 shows the MALDI-TOF spectrum of the Rituxan® standard reduced with β-mercaptoethanol (BME) where the heavy chain (m/z 50,942 Da) is completely glycosylated. Also, the rituximab heavy and light chains assembled is shown at m/z 74,178 Da as well as the dimer of the light chain at 46,196 Da. This dimer was observed in all of the MALDI spectra for the three samples. FIG. 7 shows the MALDI spectrum for the plant-made rituximab expressed alone which depicts the glycosylated heavy chain (m/z 50,698 Da) as well as non-glycosylated heavy chain (m/z 49,253 Da). Also, the rituximab heavy and light chains assembled were observed. FIG. 8 shows plant-made rituximab that was deglycosylation in planta by EndoH with reduced glycosylated heavy chain (m/z 50,687 Da) as well as in planta deglycosylated heavy chain at m/z 49,406 Da which is approximately 203 Da (molecular weight for GlcNAc) greater than that of the non-glycosylated heavy chain observed in FIG. 7. A MALDI-TOF mass spectrum for tryptic digested plant-made rituximab deglycosylated in planta with EndoH was obtained to confirm this non-glycosylated and de-glycosylated theory. A zoom of the spectrum between the mass ranges of 1100 to 1500 Da is shown in FIG. 9 where a peak was detected at 1190 Da as predicted by the theoretical tryptic digestion for the peptide containing the N-glycosylation site if it was not glycan occupied. Importantly, a peak was detected at 1393 Da, the expected mass for this peptide fragment with one GlcNAc remaining with the protein confirming that one GlcNAc remained attached to the plant-made rituximab that was deglycosylated in planta as intended.

EXAMPLE 3

In Vivo Deglycosylation of a Multi-Glycosylated Subunit Vaccine Candidate

Figure 10:
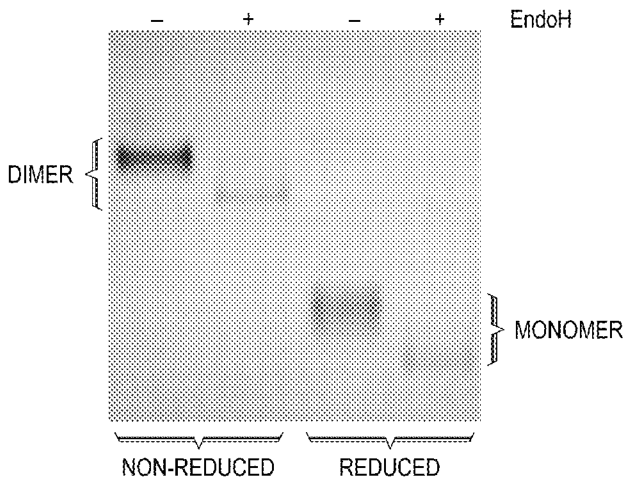
FIG. 10 shows a SDS-PAGE of E2 purified by $Ni^{2+}$-NTA originated from plant tissue expressing either E2 alone (−) or together with EndoH (+). Note the shift in molecular weight of the protein (dimer as well as monomer) when expressed with EndoH due to in planta deglycosylation.

The in vivo deglycosylation of the glycoprotein E2 from the Classical Swine Fever Virus (CSFV) was determined by co-expressing EndoH with the target protein. The CSFV E2 protein represents a different protein model as it is heavily glycosylated holding seven (7) potential N-glycosylation sites, although one N-glycosylation site is unlikely to be used since it is in close vicinity to another N-glycosylation site. Remodeling subunit vaccine protein candidates with native N-glycans found in the infected host may offer higher antigen immunogenicity thus more efficient vaccination. In order to facilitate the purification of the target protein, E2 was fused to the 6× histidine tag. E2 forms dimers when expressed in plants and the size difference between the glycosylated and potential deglycosylated E2 dimer can be easily detected on a protein gel. When E2 was expressed in plants, dimer glycoforms were produced in the expected molecular weight of about 92 kDa. However, when E2 was co-expressed with EndoH, a single dimer product was extracted at a molecular mass of about 80 kDa. The difference is mass (12 kDa) corresponds to the detached oligosaccharides (FIG. 10). The results of the SDS-PAGE showing the MM of glycosylated and deglycosylated E2 (FIG. 10) suggest that the in vivo deglycosylation of the target protein is complete.

Figure 11:
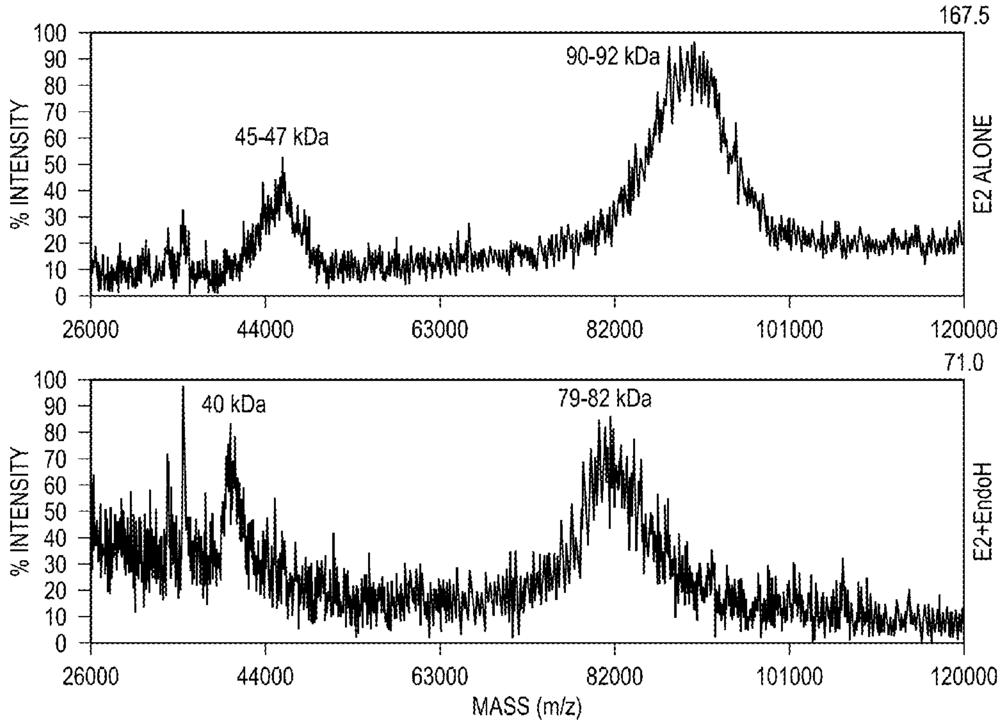
FIG. 11 shows a comparison of MALDI-TOF mass spectra of CSFV E2 either expressed alone or with EndoH in planta displaying m/z 25,000 to 120,000 mass ranges. The mass of glycosylated E2 dimer is expected to be at ~92 kDa (monomer expected to be at 46 kDa). The deglycosylated dimer is expected to be at 80 kDa (monomer expected to be at 40 kDa) if considering six N-acetylglucosamine (GlcNAc) retained on the protein.

In order to confirm the deglycosylation of E2, the masses of glycosylated and deglycosylated E2 were analyzed by MALDI TOF mass spectrometry (FIG. 11). E2 proteins were purified using nickel-chelated sepharose. The non-glycosylated E2 dimer mass is calculated at 77,400 Da (38,700 Da for the monomer). The mass of the fully glycosylated E2 dimer with high-mannose glycans is calculated to be between 90 and 95 kDa (45 and 47.5 kDa for the monomer). The mass of the deglycosylated protein with only one GlcNAc on each N-glycosylation sites is calculated at about 79,836 Da (39,918 Da for the monomer). FIG. 11 illustrates a shift of about 12 kDa in the dimer mass (6 kDa in the monomer mass) between E2 expressed alone (top panel; dimer m/z 90-92 kDa, monomer m/z 45-47 kDa) and E2 expressed with EndoH (bottom panel; dimer m/z 79-82 kDa, monomer m/z ~40 kDa). This difference corresponds to the theoretical mass of six $Man_5$ to $Man_7$ (6,084 Da to 6,804 Da per E2 monomer), the expected carbohydrate structures present on the original protein.

The present inventors successfully produced in vivo deglycosylated hIgG1, rituximab, and CSFV E2, which can then be used for in vitro reglycosylation. While the in planta deglycosylation appeared to be only partial for the hIgG1 and rituximab, however, several strategies can be implemented to optimize this in vivo protein deglycosylation step. For instance, a different expression vector combination or the generation of transgenic plants with the expression of the selected endoglycosidase under a constitutive or inducible promoter can help express the selected endoglycosidase more or/and earlier than the protein of interest to ensure complete deglycosylation.

The present invention can be used for the in vivo deglycosylation technology of other heterologous expression systems (e.g. mammalian cells, yeast and insect cells) and other recombinant protein candidates.

The present invention can be used, for example, for a wide variety of Quality-by-Design (QbD) process development in the manufacturing of therapeutics with desired glycosylation profiles, included but are not limited to: (1) production of therapeutic glycoproteins harboring human sialic acids; (2) production of therapeutic glycoprotein harboring native glycosylation patterns; (3) production of human sialylated IgG with anti-inflammatory properties; (4) production of afucosylated monoclonal antibodies with increased cytotoxicity activities; (5) increasing product homogeneity and consistency by producing signal glycoform therapeutic proteins; (6) production of rare or specific glycoforms not assembled in the current heterologous expression systems; or (7) removal of unwanted host-specific, potentially immunogenic, glycoforms.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Huang, W., Giddens, J., Fan, S., Toonstra, C., & Wang, L. (2012). Chemoenzymatic glycoengineering of intact IgG antibodies for gain of functions. Journal of the American Chemical Society, 134, 12308-12318.

Wang, L., & Lamina, J. V. (2012). Emerging technologies for making glycan-defined glycoproteins. ACS chemical biology, 7(1), 110-22.

What is claimed is:

1. A method of reducing the glycosylation of proteins comprising:

obtaining a cell that expresses one or more proteins that comprise one or more glycosylation sites and are glycosylated;

stably expressing in the cell one or more glycosidases that cleave one or more glycosyl groups from the one or more proteins to reduce the glycosylation of the protein, wherein the glycosidase cleaves one or more glycosyl groups from the one or more proteins to reduce the glycosylation of the protein; and isolating the one or more proteins with reduced glycosylation from the cell.

2. The method of claim 1, wherein the cell is a plant cell, an insect cell, yeast, or a mammalian cell.

3. The method of claim 1, wherein the one or more proteins is an antibody, an antibody fragment, a growth factor, a lymphokine, an enzyme, a receptor, a receptor binding protein, a nucleic acid binding protein, a structural protein, a pore, a channel, a kinase, a phosphatase, or a G-protein.

4. The method of claim 1, wherein the one or more glycosidases is modified recombinantly to further comprise a portion that targets the one or more glycosidases into a particular cellular compartment of protein processing that causes glycosylation of the protein, wherein the recombinantly modified glycosidase cleaves one or more glycosyl groups from the one or more proteins to reduce the glycosylation of the protein in the particular cellular compartment.

5. The method of claim 1, wherein the one or more glycosidases is modified recombinantly with a sequence that targets the glycosidase into the endoplasmic reticulum, or into vesicles past the endoplasmic reticulum, wherein the recombinantly modified glycosidase cleaves one or more glycosyl groups from the one or more proteins to reduce the glycosylation of the protein in the endoplasmic reticulum.

6. The method of claim 1, wherein the one or more glycosidases are selected from glucosides, xylanases, sialylases, lactases, amylases, chitinases, sucrases, maltases, neuraminidases, invertases, hyaluronidases and lysozymes.

7. The method of claim 1, wherein the one or more glycosidases are selected from at least one of Endoglycosidase (EndoA, EndoF1, EndoF2, EndoF3, EndoD, EndoH, EndoM, EndoS), α-N-Acetylgalactosaminidase, α1-2 Fucosidase, α1-2,3 Mannosidase, α1-3,6 Galactosidase, α2-3 Neuraminidase, β-N-Acetylhexosaminidasef, β-N-Acetylglucosaminidase, β1-3 Galactosidase, β1-4 Galactosidase, O-Glycosidase, Neuraminidase, PNGase F, PNGase A, Fetuin, O-Glycosidase, Neurominidase, β1-4 Galactosidase, or β-N-Acetylglucosaminidase.

8. The method of claim 1, wherein the cell constitutively expresses the one or more proteins, the one or more glycosidases, or both.

9. A method of reducing the glycosylation of proteins comprising:

stably co-expressing one or more proteins that comprise one or more glycosylation sites and are glycosylated in a cell with one or more glycosidases, wherein the one or more glycosidases act to reduce or eliminate the glycosylation of the one or more proteins in the cell; and purifying the one or more proteins with reduced glycosylation from the cell.

10. The method of claim 9, wherein the cell is a plant cell, an insect cell, a yeast, or a mammalian cell.

11. The method of claim 9, wherein the protein of interest is an antibody, an antibody fragment, a growth factor, a lymphokine, an enzyme, a receptor, a receptor binding protein, a nucleic acid binding protein, a structural protein, a pore, a channel, a kinase, a phosphatase, or a G-protein.

12. The method of claim 9, wherein the one or more glycosidases is modified recombinantly to further comprise a portion that targets the one or more glycosidases into a particular cellular compartment of protein processing that causes glycosylation of the protein, wherein the recombinantly modified glycosidase cleaves one or more glycosyl groups from the one or more proteins to reduce the glycosylation of the protein in the particular cellular compartment.

13. The method of claim 9, wherein the one or more glycosidases is modified recombinantly with a sequence that targets the glycosidase into the endoplasmic reticulum, or into vesicles past the endoplasmic reticulum, wherein the recombinantly modified glycosidase cleaves one or more glycosyl groups from the one or more proteins to reduce the glycosylation of the protein in the endoplasmic reticulum.

14. The method of claim 9, wherein the one or more glycosidases are selected from glucosides, xylanases, lactases, amylases, chitinases, sucrases, maltases, neuraminidases, invertases, hyaluronidases and lysozymes.

15. The method of claim 9, wherein the one or more glycosidases are selected from at least one of Endoglycosidase (EndoA, EndoF1, EndoF2, EndoF3, EndoD, EndoH, EndoM, EndoS), α-N-Acetylgalactosaminidase, α1-2 Fucosidase, α1-2,3 Mannosidase, α1-3,6 Galactosidase, α2-3 Neuraminidase, β-N-Acetylhexosaminidasef, β-N-Acetylglucosaminidase, β1-3 Galactosidase, β1-4 Galactosidase, O-Glycosidase, Neuraminidase, PNGase F, PNGase A, Fetuin, O-Glycosidase, Neurominidase, β1-4 Galactosidase, or β-N-Acetylglucosaminidase.

* * * * *